United States Patent [19]

Hsu et al.

[11] Patent Number: 4,871,357
[45] Date of Patent: Oct. 3, 1989

[54] IONIC HEPARIN COATING

[75] Inventors: Li-Chien Hsu, Mission Viejo; Sun D. Tong, Tustin, both of Calif.

[73] Assignee: Baxter International Inc., Deerfield, Ill.

[21] Appl. No.: 97,295

[22] Filed: Sep. 14, 1987

Related U.S. Application Data

[63] Continuation of Ser. No. 820,670, Jan. 21, 1986, abandoned.

[51] Int. Cl.⁴ ............................................. A61M 25/00
[52] U.S. Cl. .................................... 604/266; 604/269; 514/56; 536/21; 623/1
[58] Field of Search ................ 604/266, 268, 269; 536/21; 514/56

[56] References Cited

U.S. PATENT DOCUMENTS

| | | | |
|---|---|---|---|
| 3,522,346 | 7/1970 | Chang | 514/56 |
| 3,634,123 | 1/1972 | Eriksson et al. | 514/56 |
| 3,853,804 | 12/1974 | Yen et al. | 514/56 |
| 4,118,485 | 10/1978 | Eriksson et al. | 424/183 |
| 4,265,927 | 5/1981 | Eriksson et al. | 514/56 |
| 4,326,532 | 4/1982 | Hammar | 604/266 |
| 4,415,490 | 11/1983 | Joh | 514/56 |
| 4,565,740 | 1/1986 | Gölander et al. | 514/56 |
| 4,713,402 | 12/1987 | Solomon | 604/266 |

FOREIGN PATENT DOCUMENTS

| | | | |
|---|---|---|---|
| 2482603 | 11/1981 | France | 514/56 |
| 147696 | 11/1979 | Japan | 604/266 |
| 0136064 | 10/1980 | Japan | 604/266 |
| 0161801 | 12/1980 | Japan | 536/21 |

OTHER PUBLICATIONS

*The Merck Index*, 10th Ed., p. 150, Compound #1055, 1983.
Chem. Abstracts 104(20), 174466n.
Chem. Abstracts 96(22); 187142v.
Chem. Abstracts 77(3): 16021h.

*Primary Examiner*—Dalton L. Truluck
*Attorney, Agent, or Firm*—Michael C. Schiffer; Richard L. Myers; Paul C. Flattery

[57] ABSTRACT

A non thrombogenic quarternary ammonium/heparin complex coating for a medical article is disclosed where the organic cationic salt is an alkylbenzyldimethyl ammonium ion present in an amount of at least 50% by weight and having the following formula:

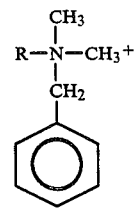

where R is a uniform alkyl group containing between 16 to 18 carbon atoms.

12 Claims, No Drawings

IONIC HEPARIN COATING

This is a continuation of co-pending application Ser. No. 820,670, filed on Jan 21, 1986, abandoned.

BACKGROUND OF THE INVENTION

In recent years great advances in medical technology have produced man made materials that make direct contact with human blood. For example, medical devices must be used in temporarily conducting the blood out of the body or used as substituted artificial organs in the body thereby necessitating the devices making direct contact with blood. Such materials include by way of example, monitoring tubes, artificial kidneys, heart valves, blood by-pass tubes and dialysis membranes.

The present state of medical technology indicates that polymers, both natural and synthetic, particularly certain synthetic plastics, have come into prominence as preferred materials for prosthetic devices. It is also known that upon contact with such materials, the blood easily coagulates and forms a thrombus or a clot on the surface of such materials. The thrombus or clot creates the serious risk of blood current blockage or, alternatively, moves along with the blood flow to cause equally dangerous complications such as pulmonary thrombosis, cerebral thrombosis or myocardial infarction.

In the use of blood contacting medical devices it has always been conventional medical practice to prevent thrombus formation by systematically administering to a patient an anticoagulant agent such as heparin, coumarine, and similar compositions. However, direct and systematic administration of these anti-coagulants also increases the risks of bleeding in a subject.

Heparin is the most well known anticoagulant and a polysaccharide not having a uniform molecular structure. It is generally considered a mixture of polymers of varying size and slight differences exist between the polymers and in the individual sugars within a particular polymer grouping. It is current expert opinion that heparin is composed of alternating derivatives of D-glucosamine (N-sulfated or N-acetylated) and uronic acid (L-iduronic acid with varying sulfate or D-glucuronic acid) joined by glycosidic linkages.

In an effort to counteract thrombogenicity and engendered bleeding, caused by direct administration of heparin, many researchers developed methods of attaching and binding heparin in the form of a coating to the walls of medical article.. Dr. Vincent Gott made the original advance in the preparation of nonthrombogenic materials by treating a graphited plastic surface with benzalkonium chloride and then with heparin. Materials treated in this way were nonthrombogenic in vitro for prolonged periods of time. Further developments followed and include that of Ericksson in U.S. Pat. No. 4,118,485, where a medical article is rendered non-thrombogenic by applying a heparin coating prepared by providing a heparin-primary amine complex and subsequently reacting the complex with a dialdehyde. While such medical research has resulted in improved stabilization of the heparinized surface, the covalant bonding which takes place with the stabilizing dialdehyde results in reduction of the physiological activity of the heparin. Additionally, such a procedure is complicated in that many steps are involved and, consequently, is relatively costly.

The binding of heparin onto a plastic polymer surface in a fully stable way has presented considerable difficulties. One major disadvantage with plastic materials coated with currently available heparin-benzalkonium complexes is that these coating complexes are unstable and subject to desorption or leaching. Consequently, in contact with biological fluids such coatings can lose up to one half of the heparin content in a period of 20 minutes. The offered explanation for this phenomena is that the ionic bonding of the anionic heparin to the cationic organic quaternary ammonium groups in the plastic surface is so unstable that heparin is continuously lost with fluid flow. Only short term applications involving blood contact of short duration can be carried out with such unstable heparinized surfaces.

Against this background it is important to find new heparin coating compositions which optimize stability and can be applied satisfactorily and consistently to a variety of materials such as natural polymers and synthetic plastics and will result in complete coverage of a medical article substrate surface with an adhesive film coating.

The present invention relates to specific a alkylbenzyldimethyl ammonium/heparin coating composition having improved surface adhesion and anti-thrombogenicity than heparin compositions heretofore known. These compositions have the distinct advantages of being relatively simple to prepare and easily applied as coatings to medical article surfaces.

SUMMARY OF THE INVENTION

In accordance with the present invention non-thrombogenic quarternary ammonium/heparin complexes are provided having in excess of fifty percent by weight of alkylbenzyldimethyl ammonium cationic ions having the formula:

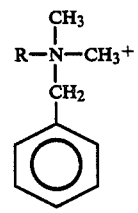

Where R is a uniform alkyl group containing between 16 to 18 carbon atoms. Additionally, methods are provided for preparing the present complex and rendering the surface of a medical article non-thrombogenic by coating the surface of such a device with the present alkylbenzyldimethyl ammonium-heparin complex. As will be discussed in detail below, surfaces of medical articles so treated with the instant heparin complex have prolonged non-thrombogenicity, improved adhesion to polymer surfaces, decreased desorption and improved biological compatability.

DETAILED DESCRIPTION OF THE INVENTION

As indicated above, the present invention relates to a hydrophobic, organic solvent soluble coating complex consisting of anionic heparin and at least 50% by weight of an alkylbenzyldimethyl ammonium cationic salt of the following formula:

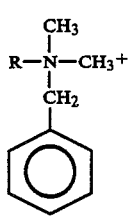

in which R is a alkyl group containing from 16 to 18 carbon atoms. When medical articles are coated with the instant heparin complex they are found to have the following characteristics when compared with presently used heparin coatings:
(1) improved adhesion and surface retention;
(2) prolonged non-thrombogenicity and decreased desorption; and
(3) optimum hydrophobicity and solubility in organic solvents.

The invention also provides a process for coating the surface of polymeric medical articles comprising:
(a) providing a medical article; and
(b) coating the medical article with a complex of anionic heparin and at least 50% by weight of an alkylbenzyl dimethyl ammonium cationic salt of the following formula:

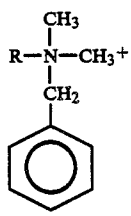

Where R is an alkyl group having from 16 to 18 carbon atoms.

The process of the instant invention further includes direct coating means of the heparin complex by straight application means as in the case of dip coating and indirect coating means as in the case of sequential applications of a cationic salt sufactant and the ionic heparin.

As is evident from the above description, there is provided a particular heparin/quarternary ammonium complex which when applied to the surface of medical articles results in a markedly improved heparinized coating. Of critical importance is the discovery herein of particular alkylbenzyl dimethyl ammonium cationic salts which can be used in high loading concentrations with heparin to form coatings having the stated beneficial features. It has been found that the present heparin/quarternary ammonium complex must have at least 50 weight percent of the organic cationic salt and preferably from 60 to 70 weight percent to achieve medical article coatings of optimum quality. Weight percent as used herein means the ratios of the quarternary ammonium moieties to the total weight of the complex. These weight percentages relate to, but are not limited by, the degrees of substitution of the cations on the heparin molecule by the cationic quarternary ammonium salt.

While all the present heparin complexes and mixtures thereof have the desired nonthrombogenic and stability characteristics, optimum and preferred results have been achieved with complexes consisting of cetalkonium heparin and/or stearylkonium heparin and mixtures thereof. It appears that the homogeneous nature of the organic cationic salt gives optimum stability and uniformity to the ultimate coating.

While not to be construed as limiting, it is speculated that the unexpected results achieved with the instant heparin/quarternary ammonium complex in conjunction with organic substrate surfaces result from the use of the particular organic salts at high concentrations. Therefore it is theorized that the longer organic chains of the cationic salt cause greater affinity to the organic substrate surface and their high concentration enhances the adhesion of the complex thereby stabilizing the heparin on the organic surface. Consequently the instant complex coating has vastly superior hydrophobicity and surface adhesion over the presently and most commonly used complexes of heparin and benzalkonium chloride.

Commercially available Benzalkonium Chloride is a mixture of alkylbenzyldimethylammonium chloride of the general formula, $[C_6H_5CH_2N(CH_3)_2 R]$ Cl, in which R represents a mixture of alkyls, including all or some of the groups comprising $C_8$ through $C_{12}$ with $C_{12}$, $Cl_{14}$ and $C_{16}$ comprising the major portion. Generally, the composition breaks down to more than 20% $C_{14}$, more than 40%, $C_{12}$ and a less than 30% mixture of $C_8$, $C_{10}$ and $C_{16}$. While the use of benzalkonium chloride/heparin complex coatings on medical articles has been effective, especially for short duration applications, they still demonstrate limited stability which is probably due to the heterogeneous nature of the mixture.

Any conventional material which makes direct contact with the blood such as glass, metals, and resins may be used as substrates within the purview of the present invention. The polymeric resin materials which serve as the substrate to be treated by the composition and processes of this invention may be any polymeric resin, natural or synthetic, conventionally used to fabricate articles commonly used in contact with blood. For example, catheters, artificial blood vessels, valves and like prosthetics are frequently fabricated from a polyethylene, polacrylic, polypropylene, polyvinyl chloride, polyamide, polyurethane, polyvinylpyrolidone, polyvinyl alcohol, cellulose acetate, polystyrene, polytetrafluroethylene, polyester such as polyethylene terephthalate, silicone rubber, natural rubber, polycarbonate and like polymeric resins and hydrogels, thereof. The resin substrate may be rigid or flexible in character, cellular or non-cellular, porous or non-porous. Also within the scope of the invention is the treatment of a coating of such a polymer resin on a metal or ceramic material.

The following examples give greater illustration and understanding of the invention.

EXAMPLE 1

27 grams of heparin was dissolved in 215 milliliters of distilled water. The solution was mixed with a 420 milliliter of a water solution containing 63 grams of purified stearylkonium chloride. This mixing was performed by stirring the heparin solution and adding the stearylkonium chloride solution to it in a drop wise manner whereby an insoluble complex of heparin and the stearylkonium chloride was formed as a precipitate. This complex compound was separated from solution by means of filtration and found to contain about 63% stearylkonium cation. The complex was found to be highly hydrophobic and had limited solubilities in polar organic solvents such as methanol, ethanol and isopropyl alcohol.

EXAMPLE 2

To illustrate the comparative characteristics of the instant heparin complexes and benzalkonium heparin, the following example and tests were carried out.

Six polyester cores generally used in arterial filters known as AF 1025 and manufactured by American Hospital Supply Corporation were provided. Two are dip coated in a 0.2%, by weight of commercially available benzalkonium heparin ("BKH") dissolved in isopropyl alcohol. Two other cores were dip coated in a 0.2%, by weight solution of stearylkonium heparin ("SKH") dissolved in of a mixture of trifluro trichloro ethane and ethanol. The two remaining cores were tested as controls.

The prepared filters along with the controls were subjected to a leaching or desorption test to determine the amount of heparin loss experienced with circulating saline liquid. The amounts and the biological activities of the respective heparin complexes on each filter were determined. The quantity of the heparin complex was ascertained by extraction with an organic solvent and the extract subjected to ultraviolet spectrophotometric analysis. The heparin biological activity test was performed utilizing a different portion of the same extracts in accordance with the Protopath Proteolytic Enzyme Detection System of American Hospital Supply Corporation.

The leaching test was carried out as follows. The saline circulation test utilized ⅜"×3/32" PVC tubing of three meters in length, a total saline volume of 1.5 liters, and the test was run at a temperature of 370° C. The saline solution was continuously circulated through the test circuit and saline samples were removed at predetermined intervals. These samples were analyzed for heparin content and activities as indicated above.

After 4 hours of saline circulation, each filter was removed and disected. 250 mls. of ethyl alcohol was then used to extract any organic coatings on the core of each filter including the control. The alcohol extract was then subjected to the UV spectrophotometric test to determine the amount of heparin complex as well as the biological activity test indicated above. The amounts and activities of heparin complexes remaining on the two sets of filters before and after saline leaching are tabulated in Tables 1 and 2. The intermittent activities of the respective saline solutions are outlined in Table 3.

Turning to Tables 1 and 2, it is evident that the Stearylkonium Heparin coating is more stable than the Benzalkonium Heparin because in excess of 80%, of the original SKH coating composition survives the saline leaching in both sets of tests whereas there is a loss of at least 85% of the BKH coatings. This is confirmed by the Heparin Activity test of the residual coatings which indicates that BKH loses a minimum of 75% of its heparin activity over the four hours of saline leaching.

The test data of Tables 1 and 2 are also important because medical devices used for blood flow are generally primed or stored in saline solutions. Consequently desorption characteristics in this medium are important in and of themselves. As one example, blood gas sensor devices used for determining types and amounts of blood gases are generally coated with heparin complexes and stored in saline. It can be appreciated from the test data that such devices coated with benzylkonium heparin will not have the requisite anti-thrombogenic quality after significant saline storage.

TABLE 1

| FIRST SET | | | | |
|---|---|---|---|---|
| | BEFORE SALINE RECIRCULATION | | AFTER 4 HRS. OF SALINE RECIRCULATION | |
| | mg BKH or SKH | HEPARIN ACTIVITY | mg BKH or SKH | HEPARIN ACTIVITY |
| 0.2% BKH COATED FILTER | 19 | 1140 | 0 (0% OF ORIGINAL) | 122 (10.7% OF ORIGINAL) |
| 0.2% SKH COATED FILTER | 19 | 875 | 16.3 (85.7% OF ORIGINAL) | 750 (85.7% OF ORIGINAL) |

TABLE 2

| SECOND SET | | | | |
|---|---|---|---|---|
| | BEFORE SALINE RECIRCULATION | | AFTER 4 HRS. OF SALINE RECIRCULATION | |
| | mg BKH or SKH | HEPARIN ACTIVITY | mg BKH or SKH | HEPARIN ACTIVITY |
| 0.2% BKH COATED FILTER | 19 | 1140 | 2.3 (12.1% OF ORIGINAL) | 271 (23.8% OF ORIGINAL) |
| 0.2% SKH COATED | 19 | 875 | 16.0 (84.2% OF ORIGINAL) | 750 (85.7% OF ORIGINAL) |

Table 3 outlines the time interval readings of the heparin activities of the circulating solutions. There is no detection (ND) of biological heparin activity during the SKH test while the BKH demonstrates an accelerated desorption within the first hour and virtual deactivation over the four hour period. This data confirms the conclusions reached with respect to Tables 1 and 2.

TABLE 3

| TOTAL HEPARIN ACTIVITY DETECTED IN CIRCULATING SALINE | | |
|---|---|---|
| | 0.2%, BKH COATED FILTER | 0.2%, SKH COATED FILTER |
| 0 TIME (AFTER PRIMING) | 240 | ND |
| 1 HOUR | 698 | ND |
| 2 HOURS | 765 | ND |
| 3¼ HOURS | 788 | ND |
| 4 HOURS | 788 | ND |

The following demonstrates the non-thrombogenic nature of SKH.

EXAMPLE 3

Fibrinogen adsorption is a known precursor to tnrombogenesis. Therefore by comparing relative amounts of Fibrinogen bound by different surfaces, predictions can be formulated on the relative thrombogenicity of an artificial blood contact material. This methodology utilizes a radiolabeled Fibrinogen which is dynamically exposed to a surface with a phosphate buffer carrier. Then by determining the radioactivity of the test samples, a relative amount of bound Fibrinogen can be determined. The Fibrinogen Adsorption Test is outlined by H. V. Roohk et al, Vol. XXIII Tran. Am.

Soc. Art. Interm Organs, 1977, P157 herein incorporated by reference. This method can be utilized as an index to evaluate and screen artificial blood contact surfaces for blood compatibility.

A medical grade PVC tubing is dip coated in 0.4% (WT/volume) SKH in a mixture of Trichloro—trifluro ethane and ethanol, subsequently dried, and sterilized by gamma radiation. The tubing sample and a control PVC tubing sample is then subjected to the Fibrinogen Adsorption Test of Roohk et al and the results set forth in Table 4. As can be appreciated there is increasing fibrinogen adsorption on the control over time and minimal Fibrinogen adsorption on the SKH coated PVC thereby demonstrating the excellent anti-thrombogenic nature of the SKH. coatings of the present invention.

TABLE 4

| PERCENTAGE OF FIBRINOGEN ADSORPTION | | |
|---|---|---|
| TIME | CONTROL PVC TUBING | SKH COATED PVC TUBING |
| 0 | 0.00 | 0.00 |
| 30 min | 0.48 | 0.22 |
| 60 min | 0.69 | 0.20 |
| 90 min | 0.74 | 0.22 |

In summary, the results of the examples and the data of tables 1, 2, 3, and 4, indicate that stearylkonium/heparin complex coatings have the following properties:
1. Superior surface adhesion in that SKH is 10 times less soluble in saline than BKH and is more hydrophobic and has higher affinity to plastic surfaces than BKH
2. Nonflammable solvent solubility (e.g. freon TE-3 5), because of the high loading of detergent thereby rendering the complex virtually non polar.
3. Improved anti-thrombogenic performance to that of BKH.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:
1. A blood contacting medical article comprising:
   (a) a substrate polymeric surface; and
   (b) an anti-thrombogenic, saline stable surface coating of a complex of heparin and at least 50% by weight of a cationic alkylbenzyl dimethyl ammonium salt having the following formula:

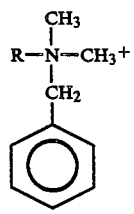

where R is an alkyl group having from 16 to 18 carbon atoms.

2. The medical article of claim 1 wherein complex is cetalkonium heparin.

3. The medical article of claim 2 wherein the complex is stearylkonium heparin.

4. The medical article of claim 1 wherein the substrate surface comprises a polymeric resin.

5. The medical article of claim 1 wherein the organic cationic salt is present in an amount of 60 to 70% by weight of the complex composition.

6. A process for rendering the polymeric surfaces of blood contacting medical articles non-thrombogenic comprising:
   (a) providing a medical article; and
   (b) coating the medical article with a complex of heparin and at least 50%, by weight of an alkylbenzyl dimethyl ammonium cationic salt of the formula:

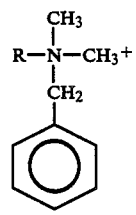

where R is an alkyl group from 16 to 18 carbon atoms.

7. The process of claim 6 wherein the coating step comprises:
   (a) providing an organic solution of the heparin complex;
   (b) applying the solution to the surface of a medical article; and
   (c) drying the medical article to form an integral adhesive coating thereon.

8. A process of claim 6 wherein the coating step comprises:
   (a) treating the medical article with a solution of a cationic quarternary ammonium organic salt having the following formula:

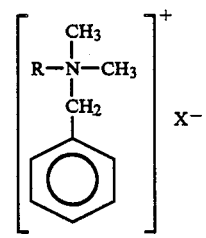

where R is an alkyl group containing from 16 to 18 carbon atoms and X is a halogen; and
   (b) subsequently treating the medical article with an aqueous solution of heparin salt.

9. A blood contacting saline stable coating comprising:
   a complex of heparin and at least 50% by weight of a cationic alkylbenzyl dimethyl ammonium salt of the formula:

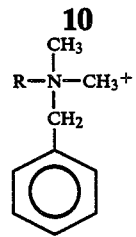
wherein:
R is a $C_{16}$ to $C_{18}$ alkyl grouping.
10. The blood contacting article of claim 9 wherein said complex is cetalkonium heparin.
11. The blood contacting article of claim 9 wherein said complex is stearylkonium heparin.
12. The blood contacting article of claim 9 wherein ammonium salt comprises from about sixty to about seventy percent by weight of the complex.
* * * * *

UNITED STATES PATENT AND TRADEMARK OFFICE
CERTIFICATE OF CORRECTION

PATENT NO. : 4,871,357

DATED : October 3, 1989

INVENTOR(S) : Li-Chien Hsu, Sun De Tong, David Paul Balding

It is certified that error appears in the above-identified patent and that said Letters Patent is hereby corrected as shown below:  ON TITLE PAGE   Item [75]

Inventor Sun D. Tong should be --Sun De Tong--

Inventor David Paul Balding should be --David P. Balding, Mission Uiejo, all of Calif.--

Signed and Sealed this

Twenty-eighth Day of April, 1992

Attest:

HARRY F. MANBECK, JR.

*Attesting Officer*    *Commissioner of Patents and Trademarks*